(12) United States Patent
Scanlan et al.

(10) Patent No.: US 11,391,718 B2
(45) Date of Patent: Jul. 19, 2022

(54) APPARATUS FOR DETERMINING VISCOELASTIC CHARACTERISTICS OF AN OBJECT, AND METHOD THEREOF

(71) Applicant: Heriot-Watt University, Edinburgh (GB)

(72) Inventors: Paul Scanlan, West Lothian (GB); Robert Lewis Reuben, Edinburgh (GB); Steven James Hammer, Edinburgh (GB); Wenmiao Shu, Edinburgh (GB); Simon Phipps, Edinburgh (GB); Stuart Alan McNeill, West Lothian (GB); Daniel W. Good, Edinburgh (GB)

(73) Assignee: HERIOT-WATT UNIVERSITY, Edinburgh (GB)

( * ) Notice: Subject to any disclaimer, the term of this patent is extended or adjusted under 35 U.S.C. 154(b) by 593 days.

(21) Appl. No.: 15/898,768

(22) Filed: Feb. 19, 2018

(65) Prior Publication Data
US 2018/0238856 A1 Aug. 23, 2018

Related U.S. Application Data

(63) Continuation of application No. 14/799,390, filed on Jul. 14, 2015, now abandoned.

(30) Foreign Application Priority Data

Sep. 4, 2014 (GB) ...................................... 1415649

(51) Int. Cl.
*G01N 33/483* (2006.01)
*A61B 5/00* (2006.01)
(52) U.S. Cl.
CPC ........ *G01N 33/4833* (2013.01); *A61B 5/0053* (2013.01); *A61B 5/4381* (2013.01); *G01N 2203/0094* (2013.01)

(58) Field of Classification Search
None
See application file for complete search history.

(56) References Cited

U.S. PATENT DOCUMENTS

| | | | | |
|---|---|---|---|---|
| 2002/0062086 A1* | 5/2002 | Miele | ................. | A61B 5/02028 600/483 |
| 2004/0034304 A1* | 2/2004 | Sumi | .................... | A61B 5/0051 600/439 |

(Continued)

FOREIGN PATENT DOCUMENTS

WO WO-2004049929 A1 6/2004

OTHER PUBLICATIONS

Phipps, S., et al., "Measurement of tissue mechanical characteristics to distinguish between benign and malignant prostatic disease," Urology, vol. 66, No. 2, Aug. 2005, pp. 447-450.

*Primary Examiner* — Matthew Kremer
(74) *Attorney, Agent, or Firm* — Nixon & Vanderhye P.C.

(57) ABSTRACT

Disclosed is an apparatus for determining viscoelastic characteristics of at least a portion of an object. The apparatus comprises a fluidly sealable housing, comprising at least one aperture and at least one fluid inlet port and at least one resilient membrane that is operatively coupled to the housing so as to sealingly engage with the at least one aperture. The apparatus further comprises at least one actuator that is operatively coupled to the at least one inlet port and adapted to actuate the at least one resilient membrane via a working fluid that is contained within the housing, so that the at least one resilient membrane is moved towards and into engagement with at least a portion of an object at a predetermined pressure. Furthermore, the apparatus comprises at least one first sensor that is operably coupled to the membrane and that is adapted to determine at least a deformation of the at least one resilient membrane during actuation.

56 Claims, 12 Drawing Sheets

(56) References Cited

U.S. PATENT DOCUMENTS

| | | | | |
|---|---|---|---|---|
| 2005/0043623 | A1* | 2/2005 | Jurvelin | A61B 8/08 600/449 |
| 2006/0051734 | A1* | 3/2006 | McNeill | A61B 5/0051 435/4 |
| 2006/0064038 | A1* | 3/2006 | Omata | A61B 5/1076 600/587 |
| 2007/0016272 | A1* | 1/2007 | Thompson | A61B 18/08 607/96 |
| 2007/0151348 | A1* | 7/2007 | Zdeblick | A61N 1/36564 73/708 |
| 2009/0076732 | A1* | 3/2009 | Sprigle | A61B 5/445 702/19 |
| 2011/0290005 | A1* | 12/2011 | Hart | G06F 19/30 73/37.9 |
| 2013/0158426 | A1* | 6/2013 | Juto | A61B 5/14539 600/552 |
| 2013/0345598 | A1* | 12/2013 | Davies | A61F 13/00 600/587 |
| 2014/0180077 | A1* | 6/2014 | Huennekens | A61B 8/12 600/425 |

* cited by examiner

APPARATUS FOR DETERMINING VISCOELASTIC CHARACTERISTICS OF AN OBJECT, AND METHOD THEREOF

CROSS-REFERENCE TO RELATED APPLICATIONS

This application is a continuation of U.S. patent application Ser. No. 14/799,390, filed on Jul. 14, 2015. U.S. patent application Ser. No. 14/799,390 claims priority from GB 1415649.1 filed on Sep. 4, 2014. U.S. patent application Ser. No. 14/799,390 and GB 1415649.1 are incorporated herein by reference in their entirety.

TECHNICAL FIELD

The present invention relates generally to the field of determining mechanical properties of an object, and in particular, to an apparatus for determining a viscoelastic characteristic of an object, and even more particularly, to an apparatus and method for determining viscoelastic characteristics of at least a portion of a soft tissue object.

INTRODUCTION

The characterisation of soft (i.e. viscoelastic) materials is required, for example, as part of various production processes and in the diagnosis of various medical conditions. In production processes, the manufacture of foams or rubber-like materials may need to be characterised in order to control the material quality and discriminate between different material types. In another example, foods may be tested to ensure its quality and freshness, wherein, in medical diagnosis, any change in the tissue characteristics may be related to the progress of a disease such as cancer, liver disease or arterial disease.

Typically, materials may be tested utilising a static palpation of at least a portion of the material under examination.

Also, it is known that diseased tissue has different static and dynamic material properties compared to healthy tissue, and these differences may be used to diagnose the type and severity of a disease. For example, in medical diagnosis, palpation is often used to "feel" pathological tissue and assess its condition. Typical examples are the palpation of breast tissue, skin tumours, digital rectal examination of the prostate and rectum, or the liver. Here, the physician simply compresses (i.e. palpates) the respective tissue with the fingers, so as to assess the tissue's mechanical characteristics, e.g. stiffness, elasticity, viscosity, motility etc.

However, static pressure palpation can be very subjective to the Examiner and is also unsuitable for providing an accurate recording of disease progression over time, therefore, significantly limiting the usefulness of the information gained from the assessment.

Furthermore, static palpation of a viscoelastic object does not provide any information on the dynamic response of that object (e.g. tissue), which has been shown to be very useful when identifying disease. The use of dynamic palpation to determine differences between a cancerous or diseased tissue and a healthy tissue is described, for example, in patent application no. US2006051734.

Accordingly, it is an object of the present invention to provide an apparatus and that is adapted to objectively determine static and/or dynamic characteristics of an object, therefore allowing an improved and objective differentiation between different material properties and/or different materials.

SUMMARY OF THE INVENTION

Preferred embodiment(s) of the invention seek to overcome one or more of the above disadvantages of the prior art.

According to a first aspect of the invention there is provided an apparatus for determining viscoelastic characteristics of at least a portion of an object, comprising:

a fluidly sealable housing, comprising at least one aperture and at least one fluid inlet port;

at least one resilient membrane, operatively coupled to said housing so as to sealingly engage with said at least one aperture;

at least one actuator, operatively coupled to said at least one inlet port and adapted to actuate said at least one resilient membrane via a working fluid contained within said housing, so that said at least one resilient membrane is moved towards and into engagement with said at least a portion of an object at a predetermined pressure, and at least one first sensor, operably coupled to said at least one resilient membrane and adapted to determine at least a deformation of said at least one resilient membrane during actuation.

This provides the advantage of an apparatus that is capable of providing an objective measurement of a dynamic response of an object to an applied dynamically controlled palpation. In particular, a sensor is directly coupled to the object engaging membrane, making it more sensitive to differences in static and dynamic mechanical properties. Also, the apparatus of the present invention provides the advantage of determining an absolute value for a mechanical characteristic of the examined material (e.g. stiffness or viscoelastic behaviour). In addition, the apparatus of the present invention is adapted to provide results independent of an examiner's subjective perception, which could differ significantly during time. Furthermore, the apparatus allows assessment of dynamic material properties, utilising dynamic actuation of the membrane when applied to the object. In addition, the apparatus of the present invention provides the advantage that its parts can be dimensioned such that the apparatus can be used in endo-cavitary applications, where palpation would not be possible when utilising the examiner's finger(s), e.g. through the urethra, using a trocar in minimally invasive surgery, or inside an artery.

Advantageously, the actuator may be adapted to selectively provide a predetermined static or transient fluid pressure within said working fluid. Even more advantageously, the actuator may be adapted to provide a predetermined pressure wave within said working fluid. Preferably, any one or all of a time period, frequency and amplitude of said pressure wave may be selectively adjustable. Even more preferably, the pressure wave may be a periodic wave. In one specific application, the predetermined pressure wave may be a square wave. This provides the advantage of being able to actuate the membrane at a variety of predetermined actuation frequencies and/or pressures, allowing the apparatus to be "tuned" to a particular material or tissue type, maximising its mechanical response and improve differentiability between different materials and/or material properties (e.g. different types of cancers in a tissue).

Advantageously, said actuator may further comprise at least one pressure sensor operably coupled to said at least one inlet port and adapted to determine the fluid pressure generated within said working fluid at said at least one inlet port during actuation. Even more advantageously, said housing may further comprise at least one force sensor operably coupled to a contact surface of said housing and adapted to determine a contact pressure when engaging said at least a portion of an object during use. Preferably, said at least one first sensor may be a strain sensor adapted to determine the strain of said at least one resilient membrane during actuation. This provides the advantage that dynamic parameters, such as the viscosity of the examined object, can be determined using, for example, phase difference between the actuator input pressure signal and the membrane response.

Advantageously, said strain sensor may comprise any one of a resistance strain gauge, an optical strain gauge, a piezoelectric sensor and a resistive pattern sensor operably printed on said at least one resilient membrane. Advantageously, said resistive pattern may be made from any one of a graphene or graphite material.

Alternatively, said at least one first sensor may be a deflection sensor adapted to determine a displacement of said at least one resilient membrane during actuation. Preferably, said deflection sensor may comprise any one of an ultrasonic transducer and an interferometer.

Alternatively, said at least one first sensor may be operably coupled to said at least one resilient membrane via a cantilever adapted to couple at least said deformation of said at least one resilient membrane with said at least one first sensor.

Advantageously, said at least one resilient membrane may comprise at least two parallelly arranged and superposed resilient layers that are bonded, so as to form said at least one resilient membrane. Preferably, said at least one first sensor may be located and secured in-between said at least two parallelly arranged and superposed resilient layers. Advantageously, said at least one resilient membrane is made from silicone. This provides the advantage that the sensor is fully protected from the environment, but still directly and operably coupled to the actuated and object-engaging membrane, therefore, providing a more accurate measurement of the membrane's deformation during actuation.

Advantageously, said housing may further comprise at least one perforated support structure operably coupled between said at least one aperture and said at least one resilient membrane, so as to form said at least one resilient membrane into a predetermined shape. Preferably, said predetermined shape may be a dome shape. This provides the advantage of preventing or minimising non-linear strain measurements, for example, when the strain gauge transitions from positive strain (fully inflated membrane) to negative strain (deflated and/or inserted membrane).

Alternatively, the apparatus may comprise a plurality of first sensors operably coupled to said at least one resilient membrane and arranged in a predetermined pattern.

Alternatively, said housing may further comprise a plurality of apertures and associated plurality of resilient membranes, and a plurality of first sensors, each operably coupled to a respective one of said associated plurality of resilient membranes. Preferably, said plurality of apertures and associated plurality of resilient membranes may be arranged in a predetermined pattern adapted to reveal movement of an object during actuation of any one of said plurality of resilient membranes during use.

Advantageously, the apparatus may further comprise a data storage adapted to receive and store data. Even more advantageously, the apparatus may further comprise a wireless transceiver adapted to transmit data from a sensor to a remote data storage.

Advantageously, said apparatus may be adapted to be transductally deployed within a cavity. Preferably, said apparatus may be removably mountable to a finger of an operator. Specifically, said object may be a biological tissue.

According to a second aspect of the invention there is provided a method for quantifying viscoelastic properties of at least a portion of an object, comprising the steps of:

(a) operably and engagingly positioning an apparatus according to claim 1 to at least a portion of an object;

(b) activating said apparatus by selectively providing a predetermined static or transient actuation pressure to said at least a portion of an object via a resilient membrane of said apparatus;

(c) recording a deformation characteristic of said resilient membrane during engagement with said at least a portion of an object;

(d) recording a contact pressure between said apparatus and said at least a portion of an object during actuation;

(e) determining at least one quantifying parameter from said deformation characteristic of said resilient membrane, utilizing said associated predetermined static or transient activation pressure and said associated contact pressure.

Advantageously, said quantifying parameter may comprise at least an elastic property of said at least a portion of an object. Even more advantageously, said quantifying parameter may further comprise at least a viscous property of said at least a portion of an object.

Advantageously, said deformation characteristic may be a strain of said membrane during activation. Alternatively, said deformation characteristic may be a deflection of said resilient membrane during activation.

Advantageously, said transient actuation pressure may comprise a transient pressure wave. Preferably, any one or all of a time period, frequency and amplitude of said pressure wave may be selectively adjustable. Alternatively, said transient actuation pressure may comprise a plurality of pressure waves, each one comprising a different predetermined frequency.

Advantageously, said method may further comprise a calibration step prior to step (a), wherein a creep-related non-linear material effect of said resilient membrane is minimised by removing the creep-related change in deformation characteristic of said resilient membrane.

Advantageously, said method may further comprise step:

(f) identifying and/or classifying a mechanical characteristic of said at least a portion of an object, utilizing said at least one quantifying parameter.

BRIEF DESCRIPTION OF THE DRAWINGS

Preferred embodiments of the present invention will now be described, by way of example only and not in any limitative sense, with reference to the accompanying drawings, in which.

DETAILED DESCRIPTION OF THE PREFERRED EMBODIMENT(S)

The exemplary embodiment(s) of this invention will be described in relation to classifying soft tissue. However, it should be appreciated that, in general, the apparatus and method of this invention will work equally well for assessing the mechanical characteristics of any other material object (such as, for example, identification of soft material types, measuring ripeness or preparedness in food production, and quality control in a production line setting for manufacture of silicone materials).

For purposes of explanation, it should be appreciated that the terms 'determine', 'calculate' and 'compute', and variations thereof, as used herein are used interchangeably and include any type of methodology, process, mathematical operation or technique. The terms 'generating' and 'adapting' are also used interchangeably describing any type of data processing.

Figure 1:
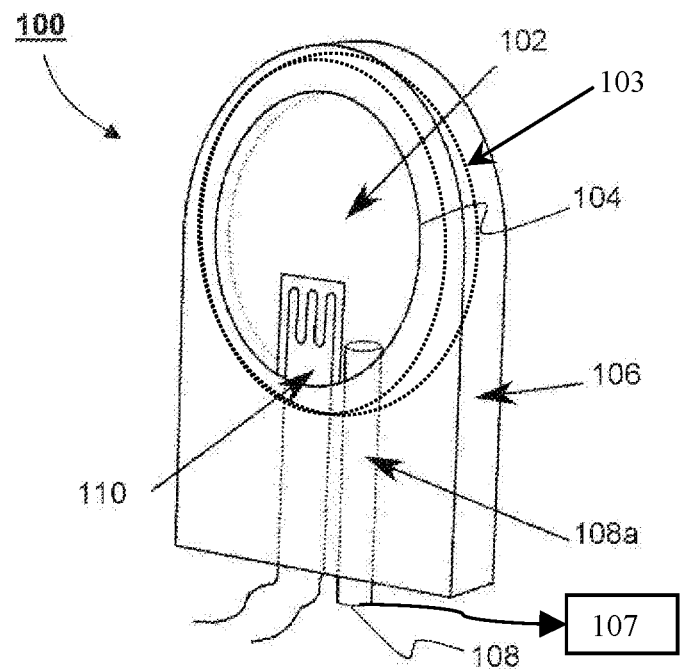
FIG. 1 shows a perspective view of a preferred embodiment of the apparatus of the present invention (called 'eFinger') utilising a single strain gauge sensor.
Figure 2:
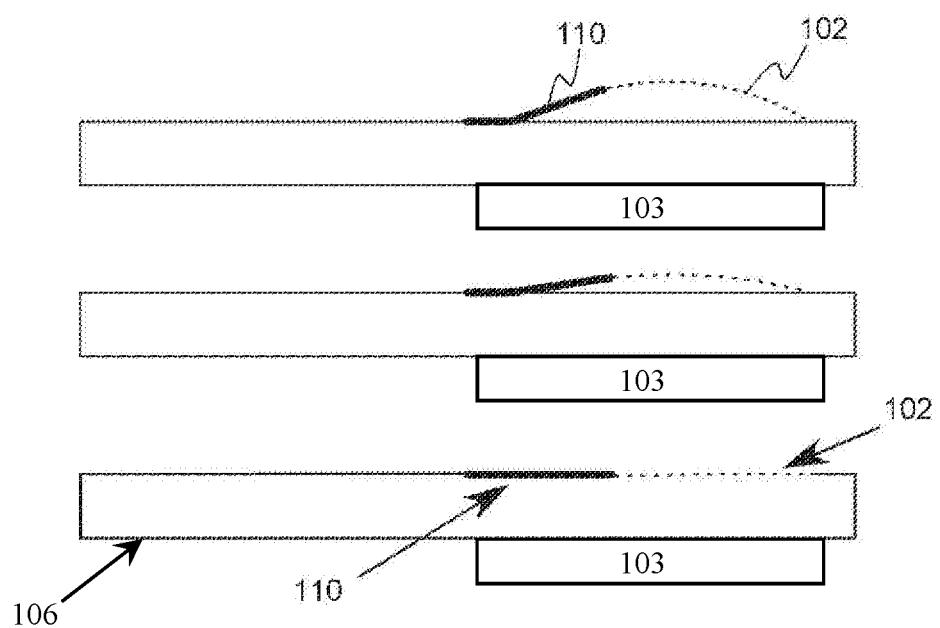
FIG. 2 shows a side-view of the apparatus shown in FIG. 1 during actuation of the membrane at a deflated state and increasingly inflated state, wherein the strain increases as the membrane inflates.

Referring now to FIGS. 1 and 2, the apparatus 100 comprises a flexible membrane 102 tensioned across an aperture 104 of a housing 106. The membrane 102, and housing 106 form a sealed fluid chamber further comprising at least one fluid inlet port 108. The fluid inlet port 108 may comprise a tubular fluid connector 108a fluidly coupling the fluid inlet port 108 and the fluid chamber, so as to allow fluid to be moved into or out of the sealed fluid chamber of the housing 106. The working fluid may be any suitable liquid or gas, for example, when used in a medical environment, the working fluid may be sterilised saline solution having predetermined mechanical properties at a predetermined temperature.

The membrane 102 may be made of at least two layered thin silicone films (not shown) that are bonded so as to form a resilient membrane of predetermined mechanical properties. Instead of the thin silicone films, any other suitable flexible material may be used fix creating the membrane 102. In the preferred embodiment of the present invention, a strain gauge 110 may be "sandwiched" between the at least two layered thin silicone films. The "sandwich" arrangement is such that it provides a fluid tight seal for the strain gauge 110, therefore, preventing any electrical contact between the working fluid and the strain gauge 110 circuitry, as well as, preventing any detachment of the strain gauge 110 from the membrane 102 during actuation. The electrical contacts of the strain gauge 110 may be embedded within the housing 106 (e.g. fluid tight channels edged into the housing structure) and coupled to an interface that is suitable for data acquisition, for example, from a computer (including signal processing means). A force sensor 103 may be coupled to a contact surface (e.g. the housing 106 surface at the membrane 102 side) of the apparatus 100, allowing the contact pressure between the apparatus 100 and the soft tissue to be measured during use. Alternatively, the force sensor 103 may be positioned on a surface of the housing that is opposite the membrane 102, therefore, measuring the contact pressure between the examiner's finger and the apparatus 100. It is understood by the person skilled in the art that the force sensor 103 can be any suitable sensor/transducer capable of determining a contact force/pressure between the contact surface and an object. In addition, a fluid pressure sensor 107 may be coupled to the inlet port 108 allowing the input fluid pressure to be determined at the fluid inlet port 108. It is also understood that the pressure sensor 107 can be any suitable sensor/transducer capable of measuring a fluid pressure.

An actuator (not shown) is coupled to the at least one inlet port 108 so as to allow actuation (i.e. pressurisation) of the working fluid within the fluid chamber of the housing 106. The actuator may be any suitable fluid pump adapted to provide a predetermined fluid flow and a predetermined fluid input pressure (static) and/or a predetermined fluid pressure wave (dynamic). The actuator may be pre-programmed and/or controlled by a computer system.

The apparatus 100 may be manufactured similar to a commonly known microfluidic chip, where layers of laser-cut PMMA material are bonded together, using contact adhesive, so as to produce a fluid-tight seal between the PMMA layers. Structural features, such as fluid channels (e.g. fluid channel from the inlet port 108 into the fluid chamber) or channels for housing the electrical contacts (cables) of the sensor, are engraved or cut into the PMMA layers. The strain gauge 110 used in the preferred embodiment of the apparatus 100 may use a Wheatstone Bridge circuit to measure the change resistance during actuation of the membrane 102. However, any other suitable circuit may be used.

The membrane 102 and corresponding housing 106, as well as, respective sensors may be dimensioned so as to suit a specific access orifice to a particular tissue area, and to also suit the size of the feature that needs to be measured. In one example embodiment, the apparatus 100 may be dimensioned so as to be suitable for access to the prostate gland via the rectum. Such an apparatus 100 may be operably placed on the examiner's finger, for example under a surgical glove to prevent contamination, and is then entered through the rectum to the area to be examined. For example, a suitable membrane 102 size may be 6 mm in diameter. However, any other suitable membrane sizes may be used, e.g. a 2 mm diameter membrane 102 may be suitable to measure the stiffness of tissue inside the urethra of an excised prostate gland.

Typical examples of material that was measured using the apparatus 100 of the present invention are:
  Gelatine samples with controlled/predetermined stiffnesses (used for calibration of the device)
  Cadaverous tissue (prostate, bladder, kidney, liver, muscle)
  Prostate glands ex vivo freshly excised following surgery
  Prostate glands in vivo palpated before surgery and accessed via the rectum.

In addition to the pressure sensor 107 coupled to the contact surface of the housing 106 on the membrane side, a pressure sensor (i.e. force-sensitive resistor) (not shown) may also be coupled to the rear of the apparatus 100 (i.e. contact surface opposite the membrane 102), therefore, allowing the pressure applied by a user's finger to be measured during use. The pressure sensor 107 may also be used to determine the reaction force from the tissue to the dynamic actuation of the membrane 102.

It is understood that the apparatus 100 of the present invention is a means of carrying out static, as well as, dynamic instrumented palpation. As shown in FIG. 2, when used in a dynamic setting, the apparatus 100 is pressed against at least a portion of an object, e.g. soft tissue, applying a predetermined controlled force (measured by the force sensor 103), and the membrane 102 is dynamically actuated, so that the force and displacement change with time (preferably in a sinusoidal fashion) and both are measured. Manipulation of the sensor outputs yields a measure of the dynamic and quasi-static behaviour of the, for example, soft tissue, and ultimately its static and dynamic modulus, which may be a function of frequency and contact pressure. The resulting measurement is a property of the tissue and, as such, can be compared with equivalent data measured in other ways (e.g. by other researchers). As a result, correlation of, for example, tissue properties with tissue condition can allow an in vivo assessment of the condition in "difficult-to-access" areas, it is understood that the apparatus 100 may be used to measure any other material e.g, foods, rubber materials, other biological matter.

Figure 3:
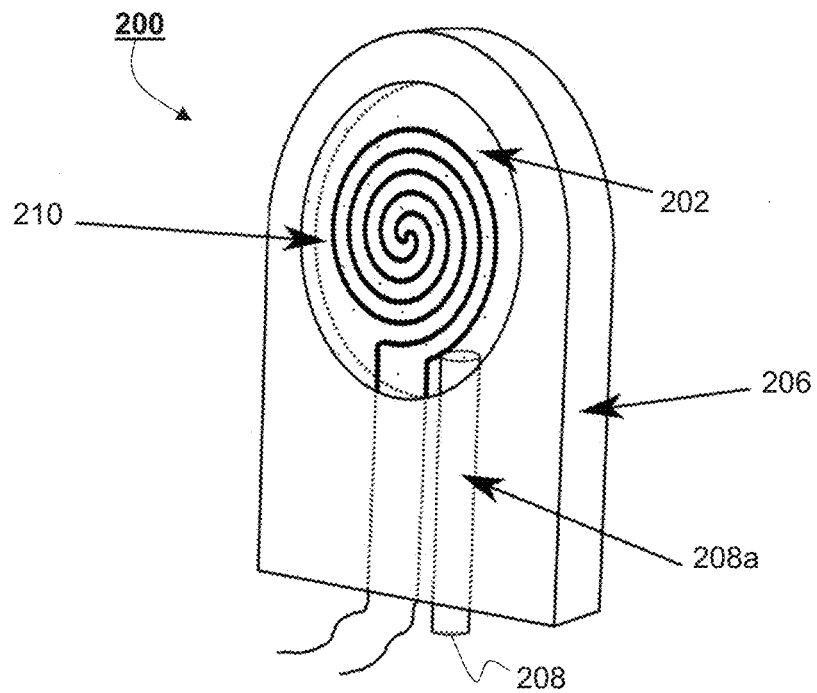
FIG. 3 shows the apparatus of FIG. 1, but with an alternative strain sensor that is embedded within, or printed onto the membrane.
Figure 4:
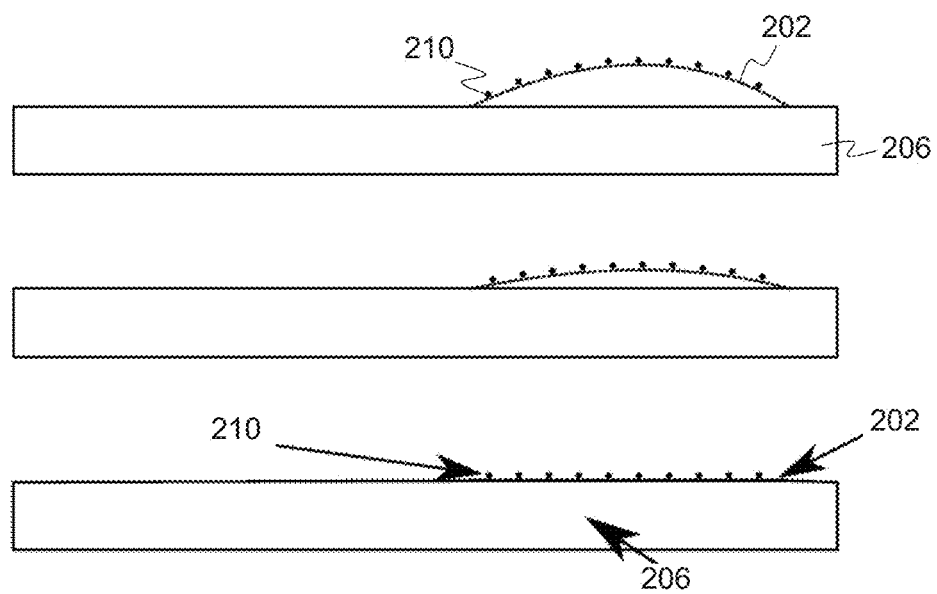
FIG. 4 shows a side-view of the apparatus of FIG. 3 during actuation of the membrane at a deflated state and increasingly inflated state, wherein the strain (and resistance of the printed pattern) increases as the membrane inflates.

Referring now to FIGS. 3 and 4, an example embodiment 200 of the present invention is shown using an alternative strain sensor 210 arrangement. In particular, the membrane 202 material may be printed with a resistive pattern. For example, a graphene or graphite pattern 210 may be printed onto the membrane 202. When using a resistive pattern 210 printed onto the surface of the membrane 202 (this may also be "sandwiched" between the at least two thin film layers of the membrane 202 to prevent fluid contamination), the pattern (e.g. graphene) flexes and contracts and its resistance changes in proportion to the inflation of the membrane 202. One of the advantages of a printed pattern 210, such as graphene, is that it is more suitable for miniaturisation than a typical resistance strain gauge 110 coupled to the membrane 102. Also, a printed pattern constrains the inflation of the membrane 202 significantly less than a strain gauge 110. The printed sensor 202 may also provide the possibility of measuring the shape of the membrane 202 rather than an average value, and is therefore potentially suitable for larger elements, which may also conform in complex ways with the surface being probed.

It is understood by the person skilled in the art that any suitable sensor or measuring principle that is capable of determining the deformation of the membrane 102, 202 can be used. For example, an optical interferometer may be utilised to measure membrane deflection instead of its strain. Furthermore, an optical strain gauge may be used to measure the membrane 102, 202 strain (e.g. with applications for use within an MRI scanner), or an ultrasonic distance measurement device may be used to measure the membrane inflation.

Alternatively, the membrane deflection/strain may be determined indirectly utilising a cantilever arrangement coupling the membrane and respective sensor. For example, a strain gauge or piezoelectric sensor may be mounted on a cantilevered arm that is attached to the membrane 102, 202. Alternatively, the piezoelectric sensor (not shown) may also be operably coupled to the membrane directly.

In another example of an alternative embodiment, a membrane support structure (not shown) may be utilised to prevent or minimise non-linear strain measurements caused when the strain gauge transitions from a positive strain (fully inflated membrane) to a negative strain (deflated and inserted membrane). For example, an internal fairing (e.g. domed structure or disc) may be placed beneath the membrane 102, 202. Here, the domed structure or disc is perforated to allow ingress of the working fluid allowing the membrane 102, 202 to be inflated. Yet, in another alternative embodiment, the membrane 102, 202, 302 may comprise pre-shaped material (e.g. created through a vacuum forming technique) allowing greater insertion into the object under examination. Additionally or alternatively, the membrane 102, 202, 302 may also comprise a portion that is stiffer than the membrane's main material, e.g. an inclusion (like a dimple) that is stiffer (less elastic) that its surrounding membrane material.

Figure 5:
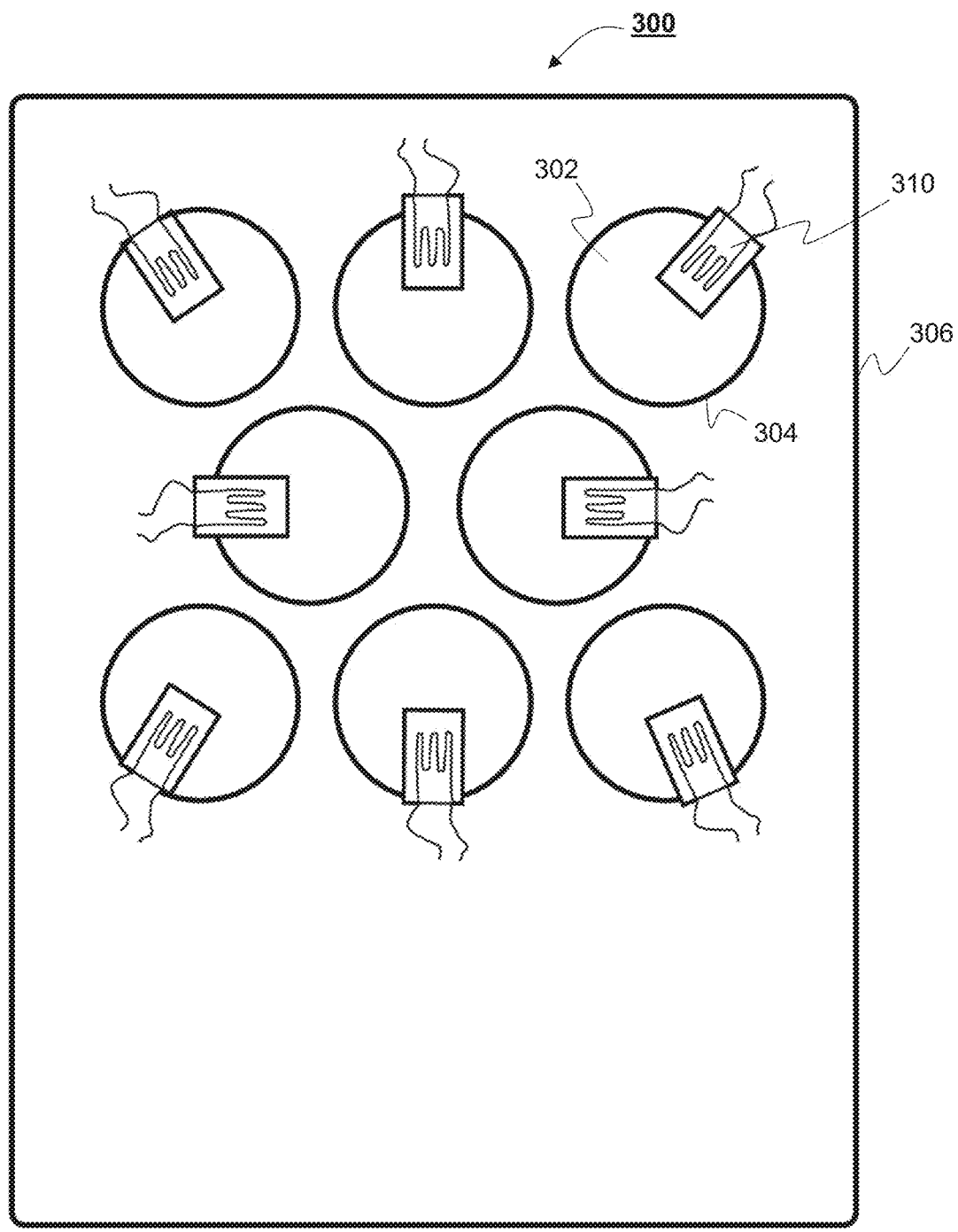
FIG. 5 shows an illustration of an example of an alternative embodiment of the apparatus of the present invention, comprising a plurality of membranes and respective strain sensors arranged in a predetermined pattern.

Referring now to FIG. 5, another alternative embodiment 300 of the present invention is shown. In particular, the housing 306 comprises a plurality of apertures 304 arranged in a predetermined pattern, as well as, corresponding membranes 302 and respective sensors 310. This embodiment 300 is adapted to provide a multi-point measurement of, for example, a soft tissue stiffness, therefore, allowing an increased spatial resolution, as well as, reduced measurement times.

Figure 6:
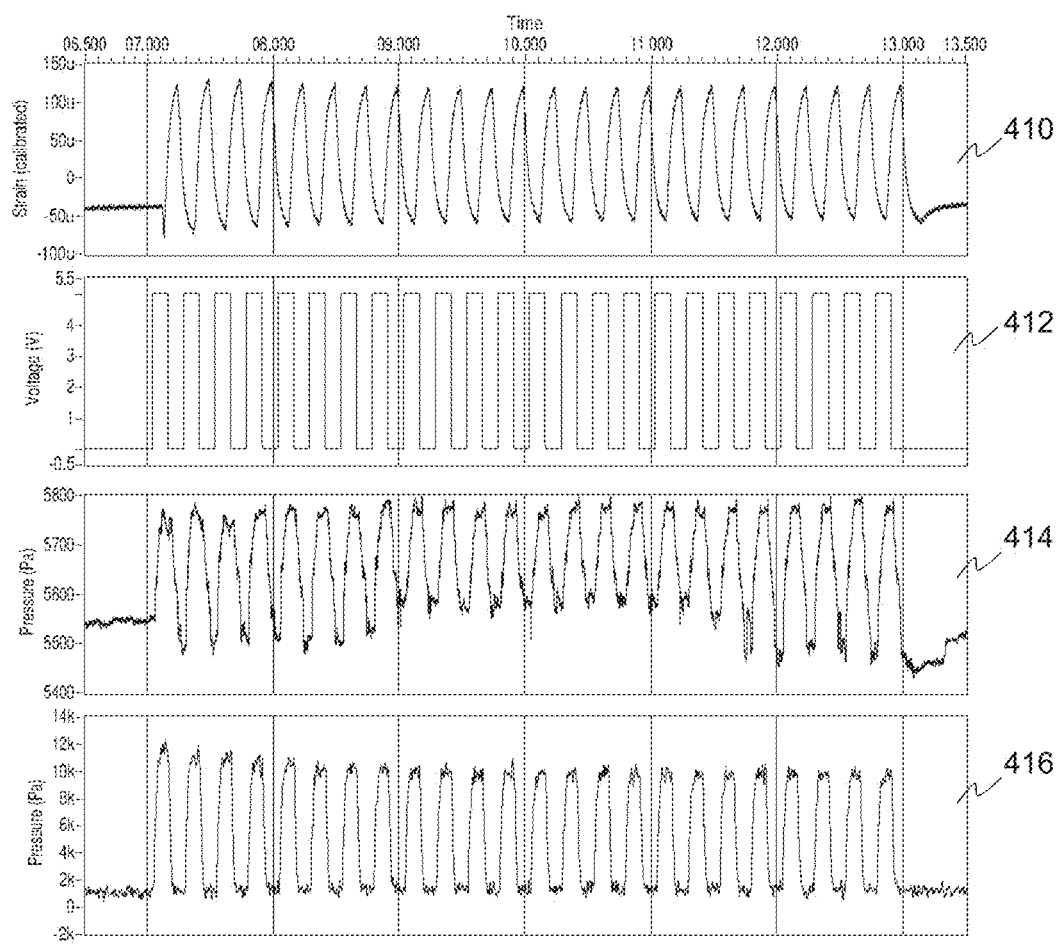
FIG. 6 illustrates graphs of the recorded output from four sensors, i.e. the membrane strain, the valve actuation signal, the applied/reaction force from the force-sensitive resistor, and the driving flow pressure signal (i.e. input pressure at the inlet port), the data is synchronised to allow phase differences to be determined.

Alternatively, a plurality of sensors 110, 210 (e.g. strain sensors or printed sensors) may be provided on a single membrane 102, 202, 302, so as to allow the measurement of the motility of tissue (and also allow multiple positions to be measured on a single, larger sensor). Sometimes during a finger palpation exam a specific tissue type can be felt to move from side to side. The use of a plurality of sensors 110, 210 on a single membrane 202, 302 would allow the movement of that particular tissue type to be measured, subsequently providing additional information about that tissue type Example of Typical Application of the Apparatus (eFinger) and Method Referring now to FIG. 6, the data from four different sensors are recorded and synchronised, the sensors are:
- a strain sensor 110, 210, 310 coupled to the membrane 102, 202, 302, measuring the combined membrane and tissue response 410 to inflation/deflation actuation;
- a valve signal 412 (e.g. from an actuator pump), which supplies a square wave signal to a solenoid valve, allowing ingress of compressed fluid (e.g. gas or liquid) into the fluid chamber of the apparatus 100;
- a force-sensitive resistor, which measures the preload pressure 414 applied to the tissue and the reaction of the tissue to the membrane 102, 202, 302 inflation
- Flow pressure signal 416, which measures the input pressure wave inflating and deflating the membrane 102, 202, 302.

The data output from the four sensors is acquired using any suitable data acquisition system. The acquisition of the data from the sensors is then synchronised so as to allow phase differences to be accurately determined.

Figure 7:
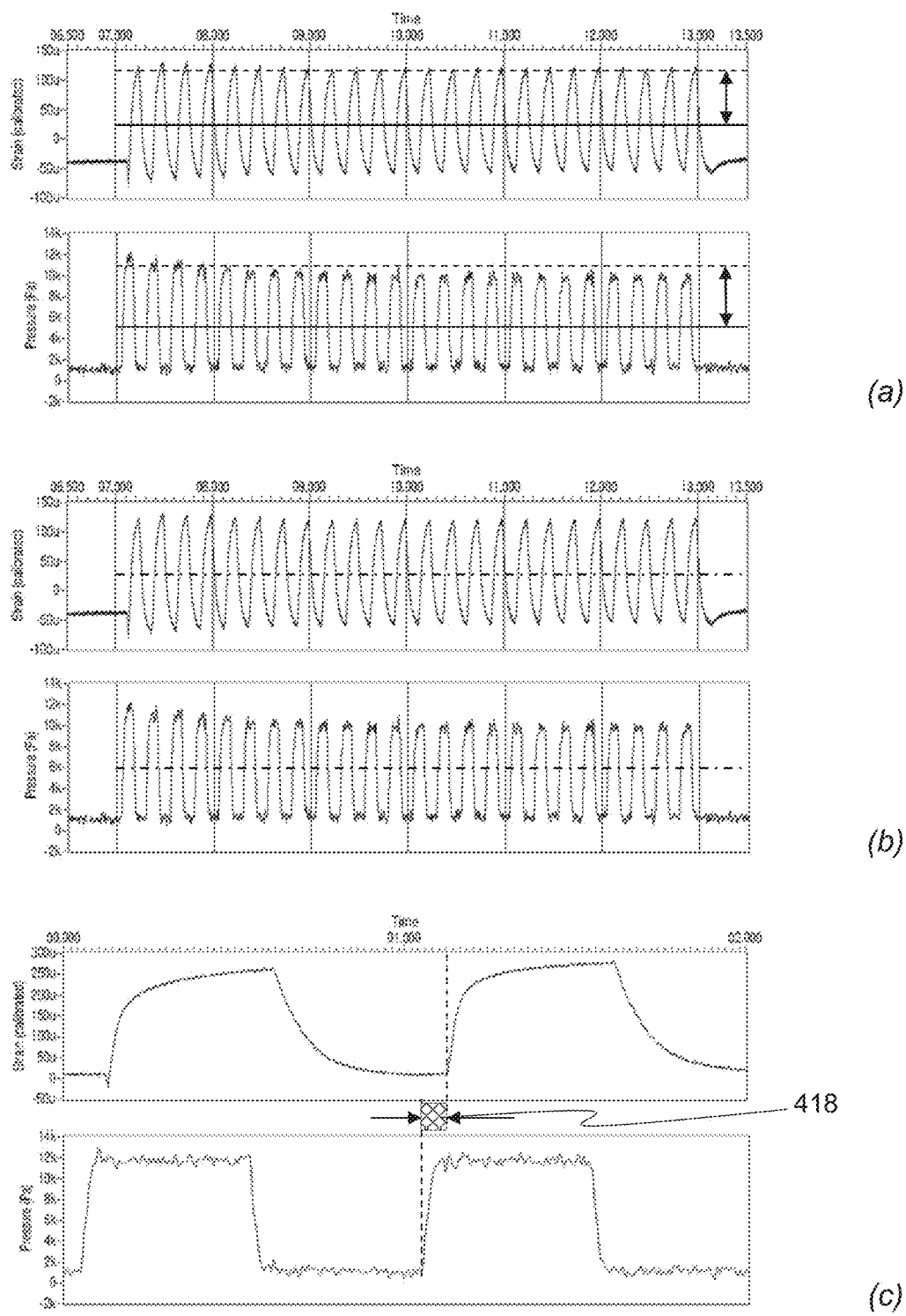
FIG. 7 (a) illustrates graphs of the membrane strain and driving flow pressure signal, of which respective amplitudes are used to calculate the amplitude ratio (AR); (b) illustrates graphs of the membrane strain and driving flow pressure signal, of which respective mean values are used to calculate the mean ratio (MR), and (c) illustrates the phase difference between the membrane strain signal and the driving flow pressure signal (i.e. input pressure at port)

As shown in FIGS. 7 (a), (b) and (c), there are three principle measurements that may be derived from the signals 410, 412, 414 and 416, which are (a) the Amplitude Ratio (AR), (b) the Mean Ratio (MR) and (c) the Phase Difference (PD).

(a) Amplitude Ratio (AR)

The amplitude ratio is defined as the amplitude of the flow sensor signal 416 divided by the amplitude of the strain signal 410. This yields the dynamic modulus of the sample being measured.

(b) Mean Ratio (MR)

The mean ratio is defined as the mean of the flow sensor signal 416 divided by the mean of the strain signal 410. This yields the quasi-static modulus of the sample being measured.

(c) Phase Difference (PD)

The phase difference 418 is the difference in signal phase (measured in radians) between the flow pressure signal 416 and the strain gauge signal 410. The phase difference 418 is related to the viscosity of the sample being measured. Typically, the tangent of the phase difference signal is used in calculations and is denoted tan(PD).

Multiple Frequency Actuation

AR, MR and PD are calculated at several different frequencies. The actuation frequency of the membrane 102, 202, 302 is easily tuneable from below 1 Hz to above 15 Hz given the suitable actuation system. Different types of tissue may show different sensitivities to different actuation frequencies, and the measure of AR, MR and PD at multiple frequencies may help to distinguish one tissue type (e.g. a more clinically significant cancer) from another tissue type (e.g. a less dangerous cancer). It may also be possible to distinguish tissue of a benign prostate hyperplasia (BPH) from tissue comprising a cancer. In order to improve efficiency of the multiple data acquisition, the actuator can be pre-programmed with a mixed frequency and the component phase lags and amplitude ratios may be recovered by Fourier analysis.

Variation of Contact Force

Another useful variable that could provide further information is the contact force. For example, increasing the contact force may allow sensing of the tissue at a deeper level, so that multiple contact forces can be used to give a three-dimensional aspect to the tissue property map.

Multiple Sensors/Sensing Positions

The use of a plurality of sensors (or a plurality of sensor positions with the same membrane) allows the acquisition of a 2D map of, for example, a particular tissue property.

Non-Steady State Signal

There is a lag at the start of the strain gauge signal 410 for many acquisitions. The signal 410 usually takes a few seconds to reach a steady state. This behaviour gives a longer-time response than the phase lag and may be used to obtain time constants for a tissue that are longer than the period of actuator modulation.

An exponential (or other, potentially multiple time-constant) curve may be fitted to the rising portion of the signal using:

$$y = a \cdot e^{-t/z} + b \qquad \text{Eq. (1)}$$

where 'a' is related to the viscous and elastic behaviour of the sample, 'b' is related to the elastic behaviour, and 'z' is related to the viscous behaviour. These values may give an indication of the type of tissue in a sample.

Apparatus Calibration (i) Dynamic and Pseudo-Static Stiffness Calibration

In order to obtain a property (e.g. dynamic modulus) from the static stiffness (force/displacement ratio), it is necessary to calibrate the apparatus 100. This is important for all embodiments of the apparatus 100, but may be more difficult for "soft" actuators, such as a gas-actuated membrane 102, 202, 302, which has inertia and rigidity that is lower than that of the material it is intended to measure.

This means that calibrating the apparatus 100 so that to provide a "real-world" stiffness value is more involved than for a rigid tipped indenter.

To calibrate the stiffness measurement of any apparatus, standardised viscoelastic gel samples (made from a gelatine/water mix) and a mechanical indenter system are utilised. A key feature of the membrane 102, 202, 302 of the apparatus 100 is its response to compression. A higher static force applied to the rear of the apparatus 100, when in use, produces a change in the "possible" expansion of the membrane and thus a change in the measured elastic modulus.

Figure 8:
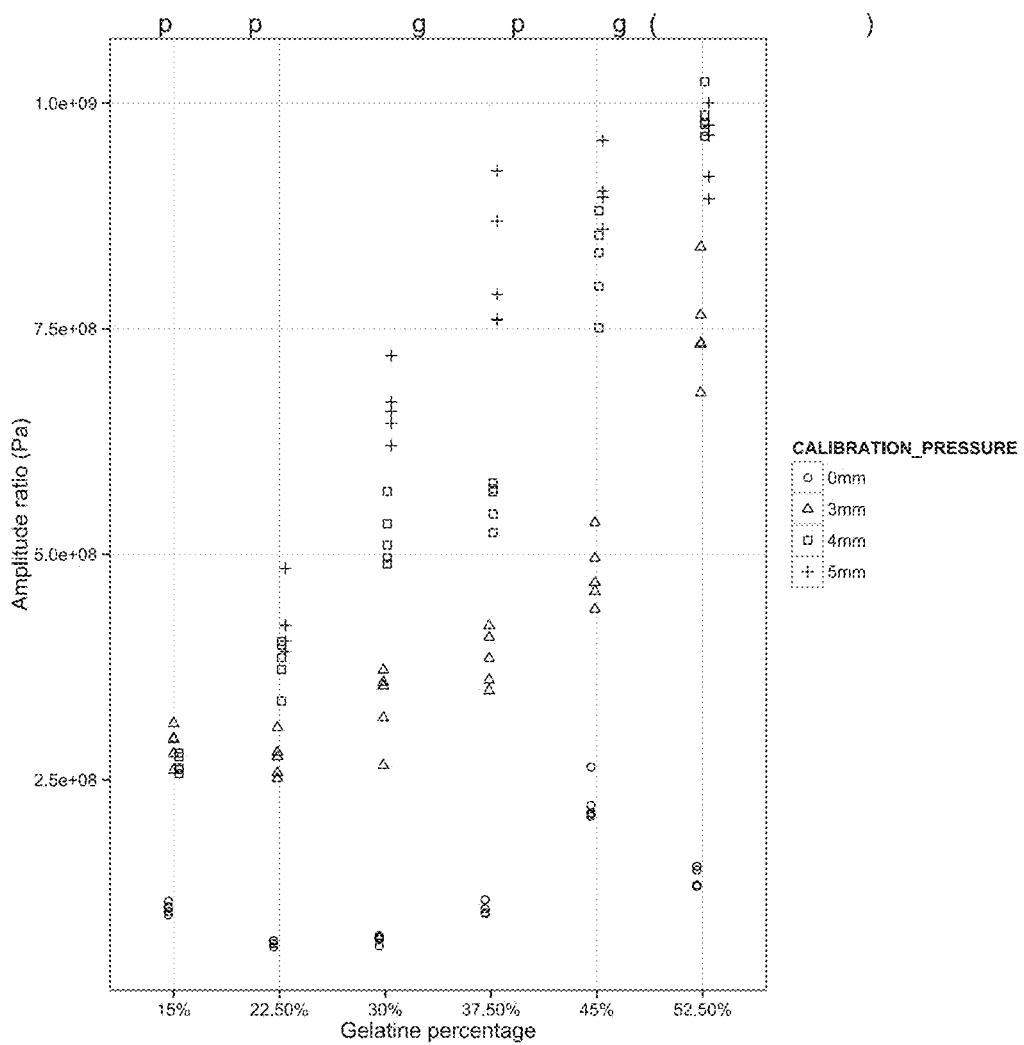
FIG. 8 shows an example calibration chart using different gelatine samples, wherein the calibration is performed at different depths of the gelatine samples, i.e. increasing the indentation depth of the membrane changes the values of AR and MR.
Figure 9:
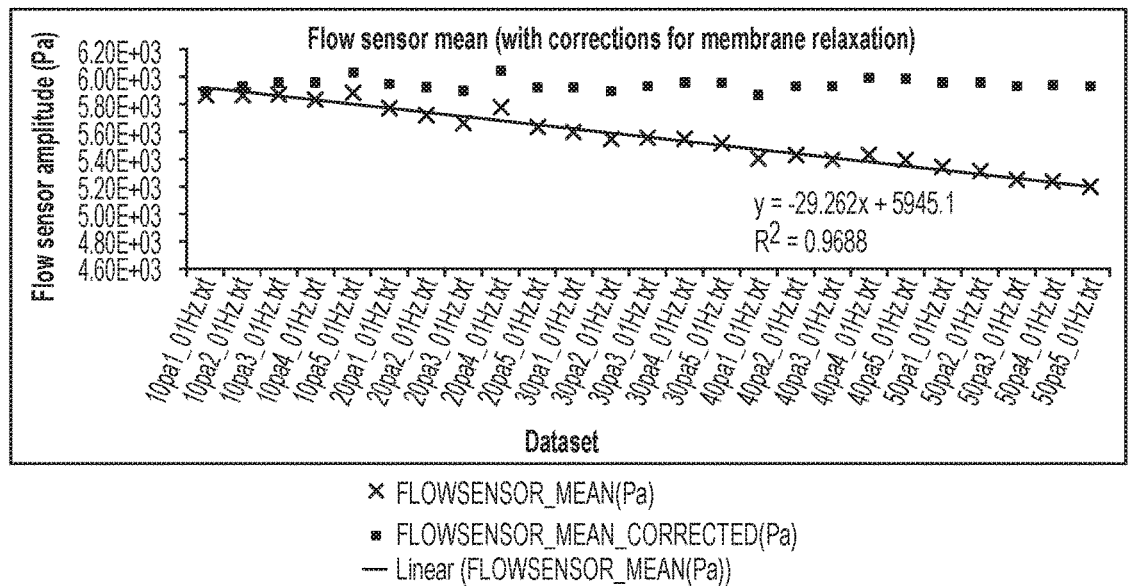
FIG. 9 illustrates a membrane relaxation calibration chart, where the mean flow pressure reduces over time as the membrane relaxes; the linear fit line may be used to compensate for the effect of membrane relaxation.
Figure 10:
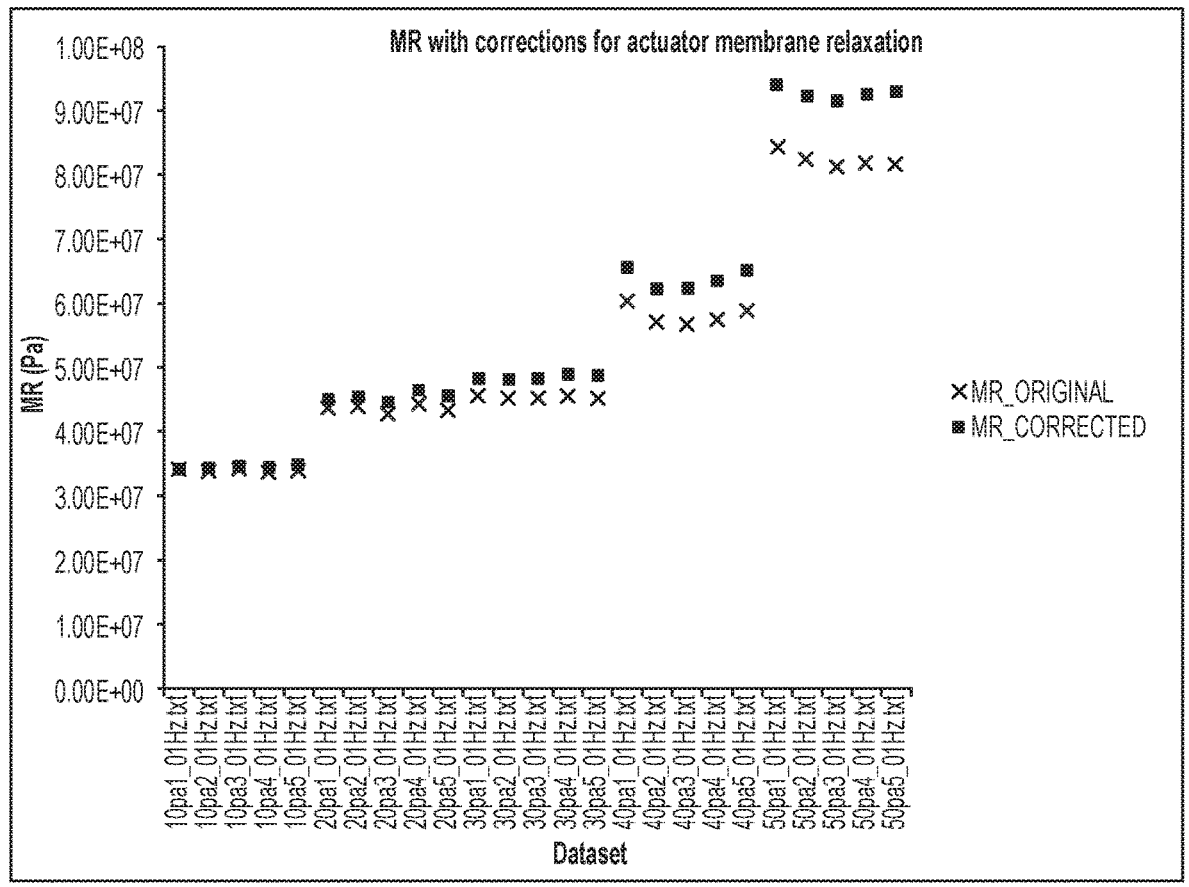
FIG. 10 shows a chart comparing the MR values corrected for the membrane relaxation with the original MR values (uncorrected)

Therefore, in this particular example, a series of gel samples were made ranging from a 15% (by volume) gel/water mix to a 52.5% (by volume) gel/water mix. The gel samples were then measured using a standardised mechanical indenter designed for measuring tissue samples. The gel samples were also measured with the apparatus 100 at a variety of controlled membrane indentation depths or static forces. The indenter was used to dynamically palpate the gel samples at a predetermined range of frequencies corresponding to those used with the apparatus 100. The resulting AR and MR obtained from the apparatus 100 were then graphed against the results from the standardised mechanical indenter and linear fit lines were created for each indentation/static force (FIG. 8). Alternatively, a fit surface may be created to allow a calibration for each driving frequency at a range of depths of penetration or applied static force.

(ii) Flexible Element Stiffness Calibration

Figure 11:
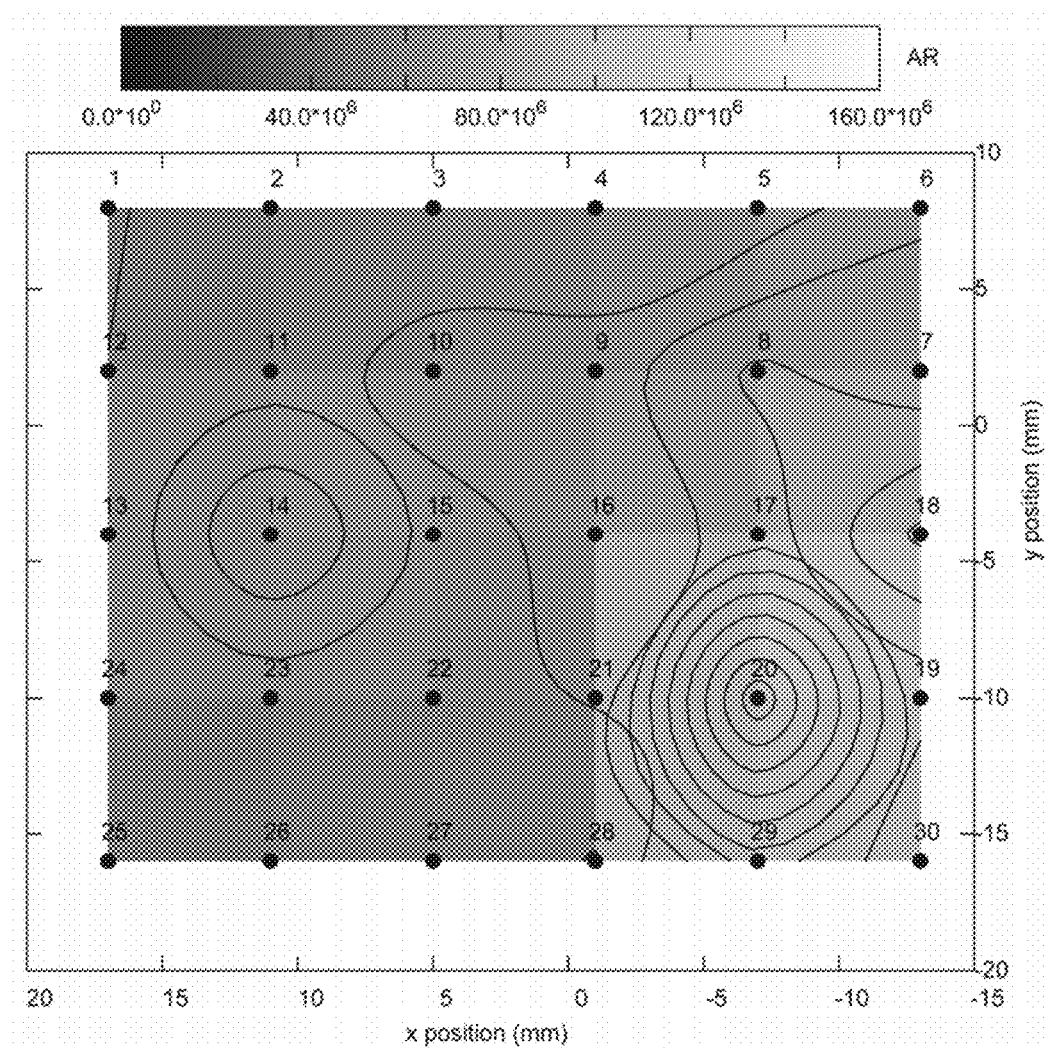
FIG. 11 illustrates a 2D contour map and greyscale map (usually in colour) showing an increase in AR across the posterior surface of an ex vivo prostate, here the decreasing spacing of the contours combined with the lighter shading show an area of high AR on the lower right-hand side of the gland.
Figure 12:
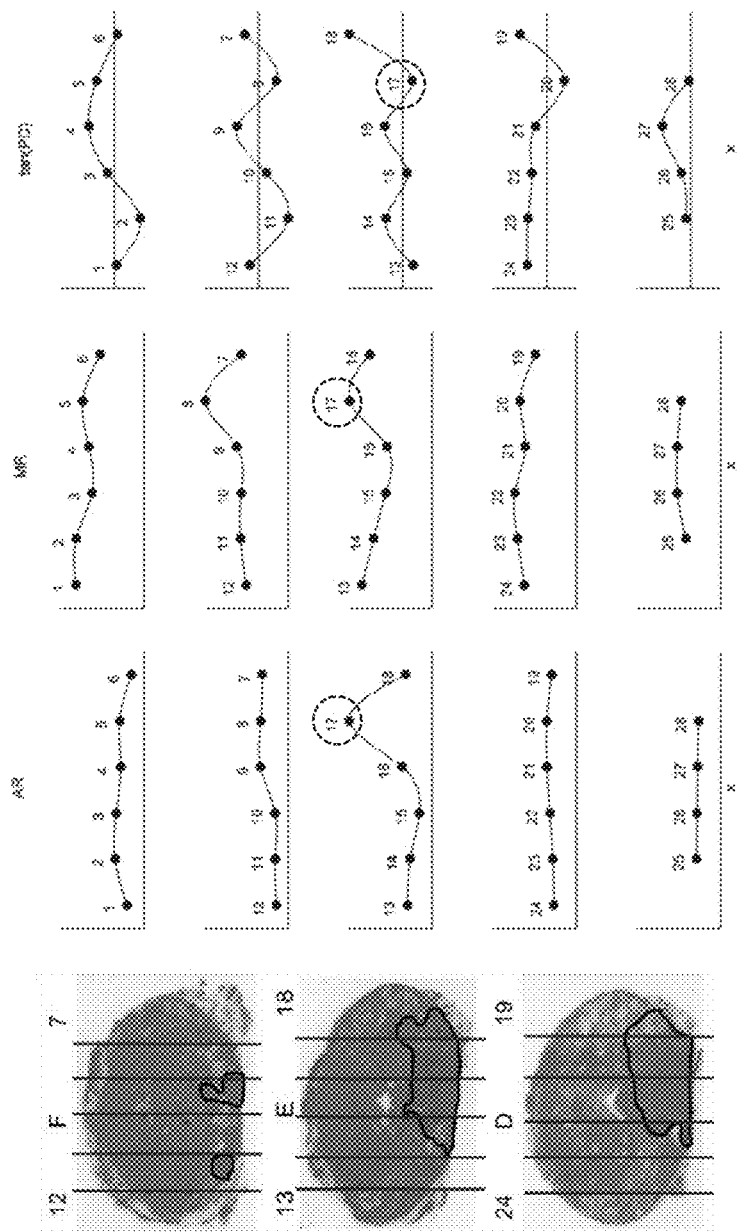
FIG. 12 illustrates ex vivo measurements of the prostate laid out in a uniformly spaced grid on the posterior surface of the gland, here the measurement portions are numbered sequentially; each line of measurements can be matched to the corresponding slice of the prostate, wherein the mechanical properties change in response to the histological status of the tissue (i.e. increased AR and MR near the tumour at position 17)

Referring now to FIGS. 11 and 12, during actuation the flexible membrane 102, 202, 302 may relax over time, losing its flexibility due to creep-related non-linear material effects. This may result in a reduction in the flow pressure 416 measured with the apparatus 100. To reduce this effect, the membrane creep effect may be removed by calculating the reduction in mean flow pressure over a set of measurements and adding this to the mean flow pressure 416. The revised MR and AR may then be calculated.

Data Interpretation

A key aspect of the apparatus 100 is the correlation between dynamic modulus and the structure of, for example, a tissue. The innovative rationale in making the measurement is that fluid-filled parts of the structure act as viscous dampers, whereas the more fibrous parts of the tissue act as springs.

(i) Using Key Mechanical Indicators to Assess Tissue Type

Referring now to FIGS. 11 and 12, AR, MR and tan(PD) may be used to identify the tissue type in each location on a sample. Typically, MR and AR are indicators of the cumulative spring stiffness of the tissue components, and tan(PD) is an indicator of the viscous component. More traditionally, the two components are termed storage modulus and loss modulus. Both the palpation frequency and the palpation depth (amount of strain) may alter one or more of the components and so the apparatus 100 yields a multi-parametric measure which can then be correlated with a multi-parametric measure of the tissue structure.

For example, for a given tissue, the probe size (i.e. palpated volume) may also affect its properties, so measurements at a range of scales can produce information at a range of tissue scales from whole organ level, through histological component level, ultimately to cell level. FIG. 12 shows an ex vivo measurement of the prostate, which are laid out in uniformly spaced grid on the posterior surface of the gland. The measurement positions are numbered sequentially and each line of measurements can be matched to the corresponding slice of the prostate. Mechanical measurements (e.g. increased AR and MR near the tumour at position 17) change the response to the histological status of the tissue.

(ii) Using Exponential Fit Parameters to Characterise Tissue Type

Figure 13:
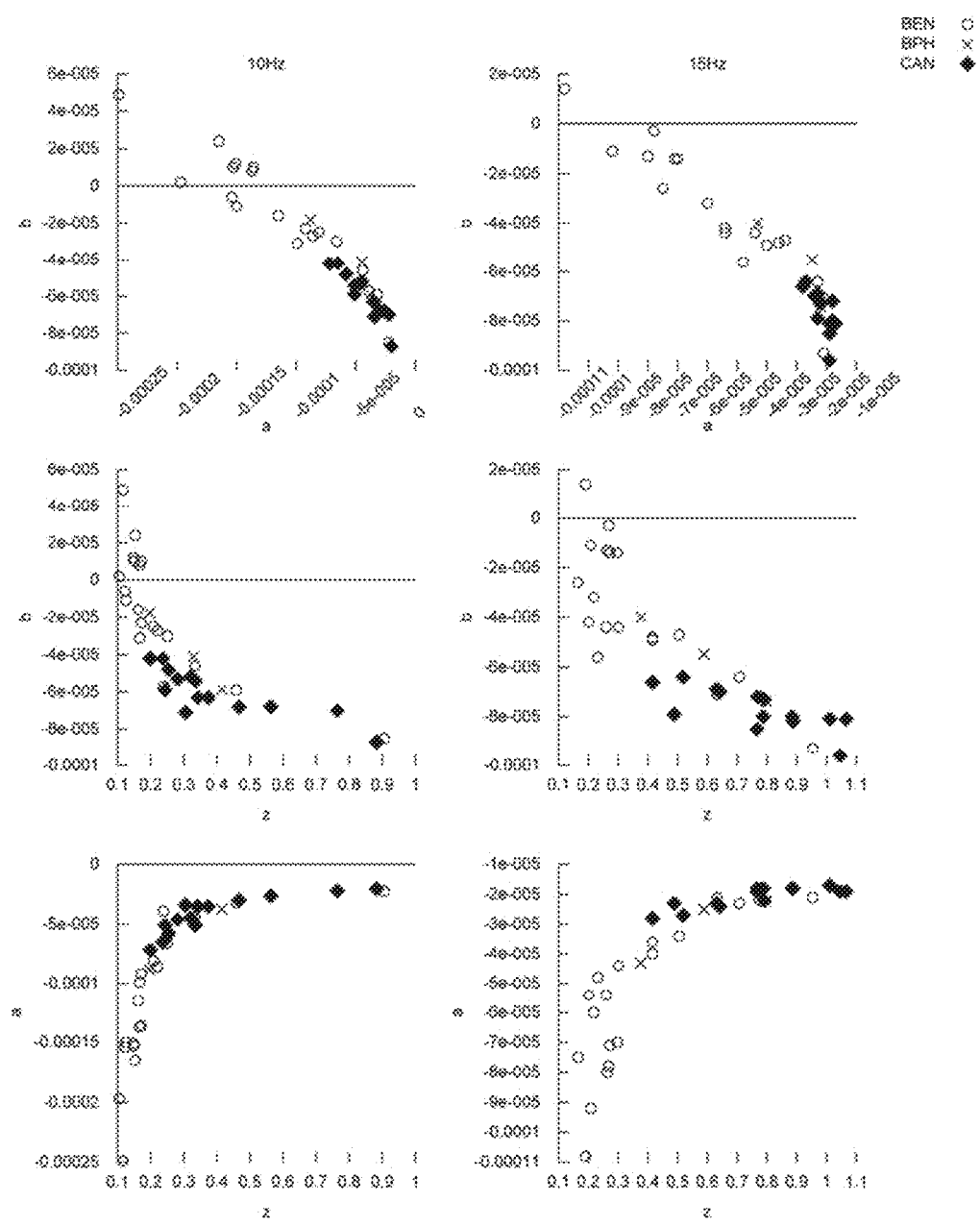
FIG. 13 illustrates a, b and z data clusters at different frequencies revealing specific tissue types (e.g. BEN-benign, CAN-cancer, BPH-benign prostate hyperplasia)

Referring now to FIG. 13, the 'a', 'b' and 'z' parameters described in Eq. (1) may be graphed together to understand their relationship to tissue type. Clusters of different tissue types may be seen that are grouped according to these values.

Figure 14:
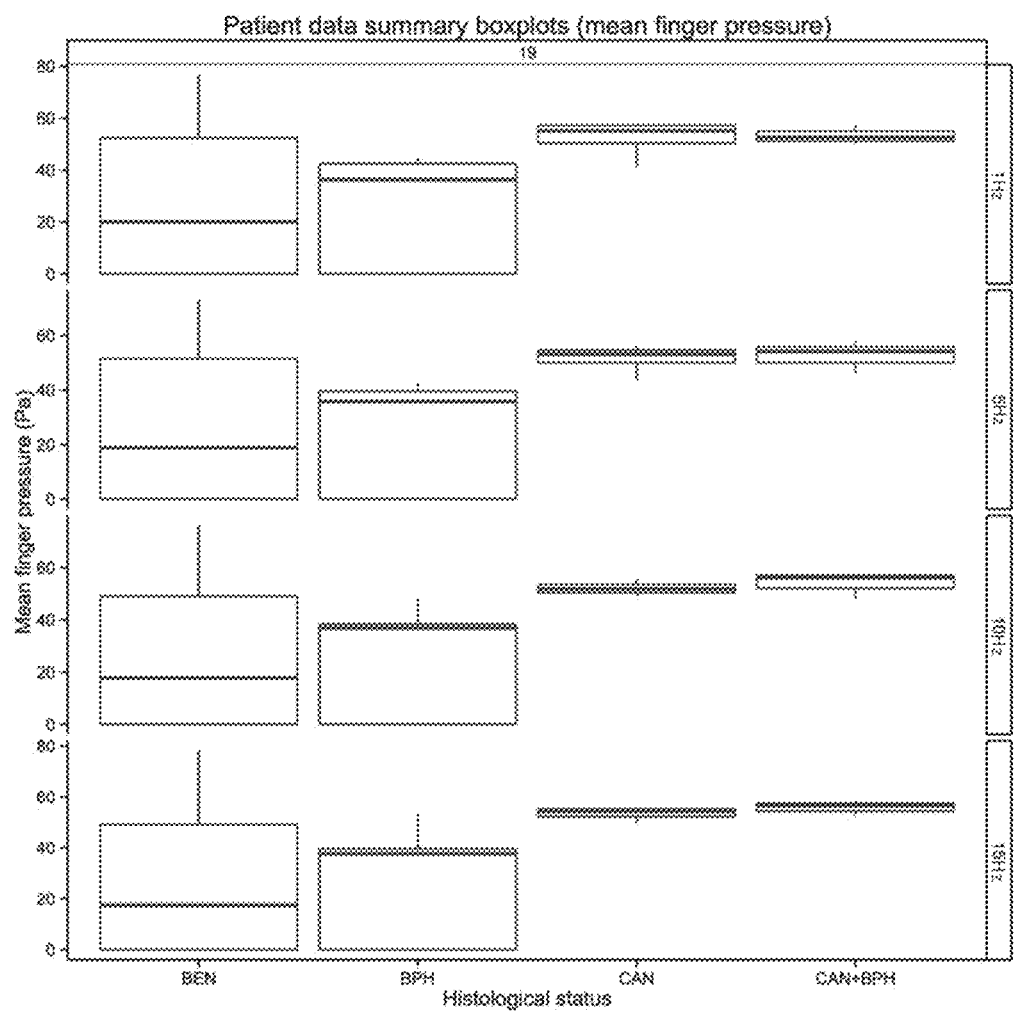
FIG. 14 is an illustration of a boxplot of mean finger pressure and reaction pressure from the tissue, revealing that changes of finger pressure may correspond to tissue classification.

(iii) Using Applied Static Pressure (Or Tissue Static Response Pressure) to Characterise Tissue Type Using a force-sensitive resistor (force sensor), the applied static pressure may be used to help distinguish tissue type. Both the mean pressure and the amplitude of the pressure response may be used to characterise the tissue type (FIG. 14).

Figure 15:
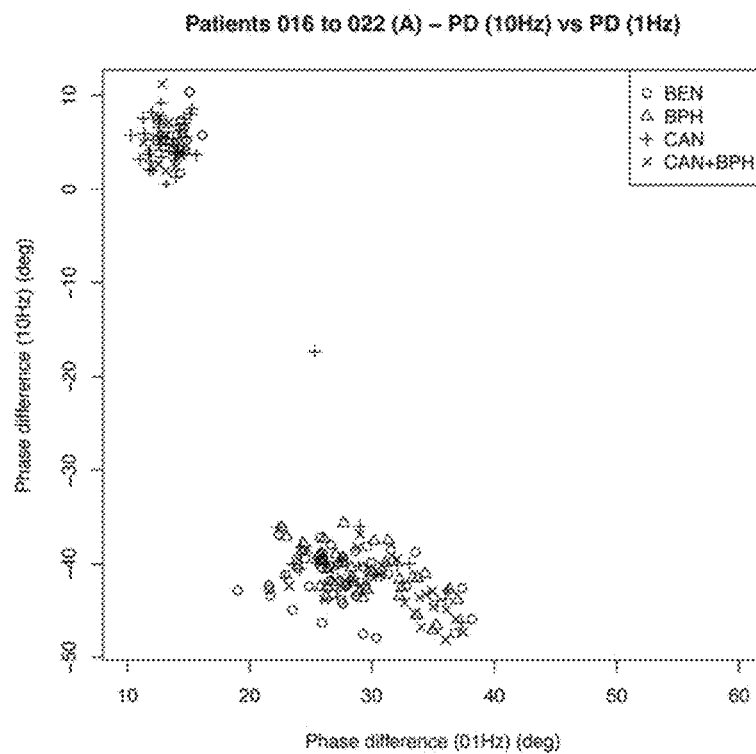
FIG. 15 illustrates phase differences at different actuation frequencies revealing a cluster of data that corresponds to different tissue types.
Figure 16:
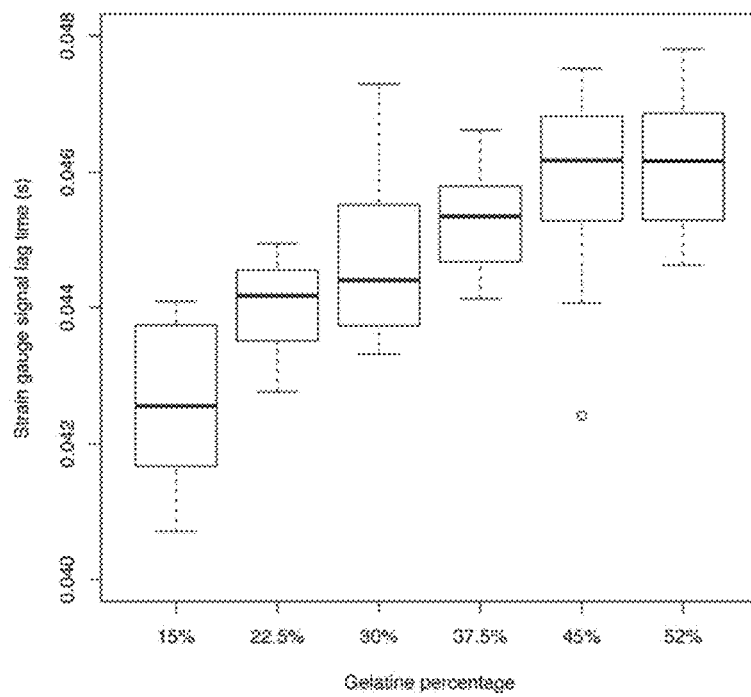
FIG. 16 illustrates a graph comparing strain-gauge-to-flow-signal lag for gelatine calibration samples at 5 Hz, wherein the signal lag between the flow signal and the strain gauge signal corresponds to changes in stiffness measured on gel calibration samples.

(iv) Multiple Frequency Properties May Be Used to Identify Different Types of Tissue The differing response of different tissue types to variations in the frequency of the membrane 102, 202, 302 actuation may be used to distinguish tissue type. In one example, the different phase-lag that tissue experiences at 1 Hz and 10 Hz actuation frequencies can be used and plotted against each other for a set of measurements taken from an ex vivo prostate gland, as shown in FIG. 15.

(v) Lag Time Between Driving Fluid Pressure Signal and Membrane Strain Signal May Distinguish Tissue Type The lag time between the start of each wave in the fluid pressure signal and the start of the corresponding wave in the strain gauge signal may be used to distinguish tissue type. The lag time increases with the stiffness of the material being measured. Stiffer materials cause a greater resistance in the membrane 102, 202, 302, causing it to take more time to inflate and deflate, and thus increase the lag relative to the flow pressure signal 416.

It will be appreciated by persons skilled in the art that the above embodiment has been described by way of example only and not in any limitative sense, and that various alterations and modifications are possible without departing from the scope of the invention as defined by the appended claims.

The invention claimed is:

1. An apparatus for quantifying viscoelastic properties of at least a portion of an object, the apparatus comprising:
   a fluidly sealable housing comprising at least one aperture and at least one fluid inlet port;
   at least one resilient membrane operatively coupled to the fluidly sealable housing so as to sealingly engage with the at least one aperture;
   at least one actuator operatively coupled to the at least one fluid inlet port and adapted to actuate the at least one resilient membrane via a working fluid contained within the fluidly sealable housing such that the at least one resilient membrane is moved towards and into engagement with the at least the portion of the object such that the apparatus is operably and engagingly positioned to the at least the portion of the object, and the at least one actuator being adapted to selectively provide a static and/or transient actuation pressure to the at least the portion of the object via the at least one resilient membrane of the apparatus;

at least one first sensor operably coupled to the at least one resilient membrane and adapted to determine at least a deformation characteristic of the at least one resilient membrane during an actuation of the actuator and during the engagement with the at least the portion of the object; and at least one force sensor operably coupled to a contact surface of the fluidly sealable housing and adapted to determine a contact force between the apparatus and the at least the portion of the object when engaging the at least the portion of the object during the actuations of the actuator and the resilient membrane;

wherein the apparatus further comprises a computer configured to determine at least one quantifying parameter of the viscoelastic properties from the deformation characteristic of the resilient membrane, utilizing the static and/or transient actuation pressure and the contact force; and wherein the apparatus further comprises a pressure sensor configured to measure a contact pressure between an examiner's finger and the apparatus.

2. The apparatus of claim 1, wherein the actuator is adapted to provide a pressure wave within the working fluid, with any one or all of a time period, frequency and amplitude of the pressure wave being selectively adjustable, so as to provide the static and/or transiet actuation pressure.

3. The apparatus of claim 2, wherein the pressure wave is a periodic wave.

4. The apparatus of claim 2, wherein the pressure wave is a periodic square wave.

5. The apparatus of claim 1, wherein the actuator comprises at least one pressure sensor operably coupled to the at least one fluid inlet port and adapted to determine fluid pressure generated within the working fluid at the at least one fluid inlet port during the actuation of the actuator.

6. The apparatus of claim 5, wherein the at least one first sensor comprises any one of a resistance strain gauge, an optical interferometer, a piezoelectric sensor and a resistive pattern sensor having a resistive pattern operably printed on the at least one resilient membrane, the resistive pattern made from any one of a graphene or graphite material.

7. The apparatus of claim 1, wherein the at least one first sensor is a deflection sensor adapted to determine a displacement of the at least one resilient membrane, as the deformation characteristic, during the actuation of the actuator.

8. The apparatus of claim 1, wherein the at least one first sensor is operably coupled to the at least one resilient membrane via a cantilever adapted to couple at least the deformation of the at least one resilient membrane with the at least one first sensor.

9. The apparatus of claim 1, wherein the at least one resilient membrane comprises at least two parallel and superposed resilient layers that are bonded so as to form the at least one resilient membrane, and wherein the at least one first sensor is located and secured in-between the at least two parallel and superposed resilient layers.

10. The apparatus of claim 1, wherein the fluidly sealable housing comprises at least one perforated support structure operably coupled between the at least one aperture and the at least one resilient membrane so as to form the at least one resilient membrane into a shape.

11. The apparatus of claim 1, comprising a plurality of first sensors operably coupled to the at least one resilient membrane and arranged in a pattern.

12. The apparatus of claim 1, wherein the fluidly sealable housing comprises a plurality of apertures and associated plurality of resilient membranes, and a plurality of first sensors, each operably coupled to a respective one of the associated plurality of resilient membranes, the plurality of apertures and associated plurality of resilient membranes are arranged in a pattern adapted to reveal movement of the object during an actuation of any one of the plurality of resilient membranes during use.

13. The apparatus of claim 1, comprising any one of a data storage, adapted to receive and store data from the at least one first sensor and/or the at least one force sensor, and a wireless transceiver, adapted to transmit the data from the at least one first sensor and/or the at least one force sensor to a remote data storage.

14. The apparatus of claim 1, wherein the apparatus comprises a finger contact surface opposite the membrane and is thereby removably mountable to the examiner's finger, and wherein the apparatus is transductally deployable.

15. The apparatus of claim 1, wherein the working fluid is a liquid.

16. The apparatus of claim 1, wherein the computer is configured to synchronize data from at least two of the first sensor, the force sensor and the pressure sensor to allow phase differences of the data from the at least two of the first sensor, the force sensor and the pressure sensor to be calculated and to thereby calculate the at least one quantifying parameter.

17. The apparatus of claim 1, wherein the viscoelastic properties comprise a viscous property of the at least the portion of the object.

18. The apparatus of claim 1, wherein the viscoelastic properties comprise a dynamic mechanical property of the at least the portion of the object.

19. The apparatus of claim 1, further comprising a perforated support structure coupled between the at least one aperture and the at least one membrane to form the at least one resilient membrane into a dome shape.

20. The apparatus of claim 1, wherein the actuator is adapted to provide a static pressure and a periodic dynamic pressure wave as the static and/or transient actuation pressure.

21. The apparatus of claim 1, configured such that when at least a part of the apparatus is pressed against the at least the portion of the object, the membrane is dynamically actuated by the at least one actuator so that changes of the membrane with time are measured.

22. The apparatus of claim 1, wherein the object is soft tissue and the computer is further configured to measure dynamic and quasi-static behavior of the soft tissue as the at least one quantifying parameter of the viscoelastic properties of the at least the portion of the object.

23. The apparatus of claim 22, wherein the computer is further configured to measure the dynamic and quasi-static behavior of the soft tissue as a function of a frequency of a pressure wave of the transient actuation pressure and the contact force between the apparatus and the at least the portion of he object.

24. The apparatus of claim 1, wherein the object is soft tissue and the computer is further configured to measure static and dynamic moduli of the soft tissue as the at least one quantifying parameter of the viscoelastic properties of the at least the portion of the object.

25. The apparatus of claim 1, further comprising a membrane support structure.

26. The apparatus of claim 1, wherein the at least one first sensor comprises a strain sensor coupled to the membrane and configured to measure a combined response of the at least one resilient membrane and the at least the portion of the object to inflation and deflation actuation of the at least one resilient membrane to determine the deformation characteristic of the at least one resilient membrane based on the combined response.

27. The apparatus of claim 1, wherein the computer is adapted to calculate an amplitude ratio of an amplitude of a flow pressure signal and an amplitude of a signal of the at least one force sensor, the flow pressure signal corresponding to an input pressure wave inflating and deflating the at least one resilient membrane, and the signal of the at least one force sensor being used to determine the contact force between the apparatus and the at least the portion of the object when engaging the at least the portion of the obeject during the actuations of the actuator and the resilient membrane.

28. The apparatus of claim 1, wherein the computer is adapted to distinguish a tissue type of the object from the at least one quantifying parameter.

29. The apparatus of claim 1, wherein the object is a prostate gland.

30. A method for quantifying viscoelastic properties of at least a portion of an object, the method comprising:
    (a) operably and engagingly positioning an apparatus to the at least the portion of the object;
    (b) activating the apparatus by selectively providing a static and/or transient actuation pressure to the at least the portion of the object via a resilient membrane of the apparatus;
    (c) recording a deformation characteristic of the resilient membrane during engagement with the at least the portion of the object;
    (d) recording a contact force between the apparatus and the at least the portion of the object during actuation of the resilient membrane using a force sensor, the actuation of the resilient membrane being provided as a result of the activating of the apparatus; and
    (e) determining at least one quantifying parameter of the viscoelastic properties from the deformation characteristic of the resilient membrane, utilizing the static and/or transient actuation pressure and the contact force;
    the method further comprising measuring a contact pressure between an examiner's finger and the apparatus.

31. The method of claim 30, wherein the at least one quantifying parameter comprises at least an elastic property and/or a viscous property of the at least the portion of the object.

32. The method of claim 30, wherein the deformation characteristic is a strain of the resilient membrane during the actuation of the resilient membrane.

33. The method of claim 32, wherein the strain is measured during the actuation of the resilient membrane.

34. The method of claim 30, wherein the deformation characteristic is a deflection of the resilient membrane during the actuation of the resilient membrane.

35. The method of claim 30, wherein the transient actuation pressure comprises a transient pressure wave of which any one or all of its time period, frequency and amplitude is selectively adjustable.

36. The method of claim 30, wherein the transient actuation pressure comprises a plurality of pressure waves, each one comprising a different frequency.

37. The method of claim 30, comprising a calibration step prior to step (a), wherein a creep-related non-linear material effect of the resilient membrane is minimized by removing a creep-related change in the deformation characteristic of the resilient membrane.

38. The method of claim 30, comprising:
    (f) identifying and/or classifying a mechanical characteristic of the at least the portion of the object, utilizing the at least one quantifying parameter.

39. The method of claim 30, wherein the activating of the apparatus includes the actuation of the resilient membrane, and the actuation of the resilient membrane is performed by at least one actuator via a working fluid which is a liquid.

40. The method of claim 39, wherein the at least one quantifying parameter is calculated from a phase difference between an actuator input pressure signal and a response signal of the at least one resilient membrane used for determining the deformation characteristic of the at least one resilient membrane, wherein the actuator input pressure signal, as the static and/or transient actuation pressure, corresponds to an input pressure wave for inflating and deflating the at least one resilient membrane.

41. The method of claim 30, wherein the at least one quantifying parameter which is determined is a viscous property of the at least the portion of the object.

42. The method of claim 30, wherein the at least one quantifying parameter which is determined is a dynamic mechanical property of the at least the portion of the object.

43. The method of claim 30, wherein the activating of the apparatus includes the actuation of the resilient membrane at a variety of actuation frequencies and/or actuation pressures to differentiate between different materials and/or material properties.

44. The method of claim 30, wherein providing the static and/or transient actuation pressure comprises the step of providing both a static pressure and a periodic dynamic pressure wave.

45. The method of claim 30, wherein: when at least a part of the apparatus is pressed against the at least the portion of the object, the activating of the apparatus comprises the actuation of the resilient membrane so that changes of the membrane with time are measured.

46. The method of claim 30, wherein the object is soft tissue and the determining of the at least one quantifying parameter of the viscoelastic properties of the at least the portion of the object includes measuring dynamic and quasi-static behavior of soft tissue as the at least one quantifying parameter of the viscoelastic properties of the at least the portion of the object.

47. The method of claim 46, wherein the dynamic and quasi-static behavior of the soft tissue is measured as a function of a frequency of a pressure wave of the transient actuation pressure and contact force between the apparatus and the at least the portion of the object.

48. The method of claim 30, wherein the object is soft tissue and the determining of the at least one quantifying parameter of the viscoelastic properties of the at least the portion of the object includes measuring static and dynamic moduli of the soft tissue as the at least one quantifying parameter of the viscoelastic properties of the at least the portion of the object.

49. The method of claim 30, further comprising calculating an amplitude ratio of an amplitude of a flow pressure signal and an amplitude of a signal of the at least one force sensor to determine the at least one quantifying parameter of the viscoelastic properties of the at least the portion of the object, the flow pressure signal, as the static and/or transient actuation pressure, corresponding to an input pressure wave inflating and deflating the at least one resilient membrane, and the signal of the at least one force sensor being used to determine the contact force between the apparatus and the at least the portion of the object when engaging the at least the portion of the object during the actuation of the resilient membrane.

50. The method of claim 30, further comprising varying the contact force to give a three dimensional aspect to a measured tissue property of the object in the determining of the at least one quantifying parameter of the viscoelastic properties of the object.

51. The method of claim 30, wherein:
the recording of the deformation characteristic of the resilient membrane is performed with a strain gauge, and
behavior of a signal from the strain gauge is processed to obtain time constants for the object which are longer than a period of actuator modulation during which an actuator provides the static and/or transient actuation pressure to activate the apparatus.

52. The method of claim 30, wherein the object comprises tissue and a dynamic modulus of tissue that is correlated with tissue structure and is determined from the at least one quantifying parameter.

53. The method of claim 30, wherein the object comprises tissue and the method comprises distinguishing tissue type using the at least one quantifying parameter.

54. The method of claim 30, wherein the object is a prostate gland.

55. An apparatus for quantifying viscoelastic properties of at least a portion of an object, the apparatus comprising:
a fluidly sealable housing comprising at least one aperture and at least one fluid inlet port;
at least one resilient membrane operatively coupled to the fluidly sealable housing so as to sealingly engage with the at least one aperture;
at least one actuator operatively coupled to the at least one fluid inlet port and adapted to actuate the at least one resilient membrane via a working fluid contained within the fluidly sealable housing such that the at least one resilient membrane is moved towards and into engagement with the at least the portion of the object such that the apparatus is operably and engagingly positioned to the at least the portion of the object, and the at least one actuator being adapted to selectively provide a static and/or transient actuation pressure to the at least the portion of the object via the at least one resilient membrane of the apparatus;
at least one first sensor operably coupled to the at least one resilient membrane and adapted to determine at least a deformation characteristic of the at least one resilient membrane during an actuation of the actuator and during the engagement with the at least the portion of the object; and
at least one force sensor operably coupled to a contact surface of the fluidly sealable housing and adapted to determine a contact force between the apparatus and the at least the portion of the object when engaging the at least the portion of the object during the actuation of the actuator;

wherein the apparatus further comprises a computer configured to:
determine at least one quantifying parameter of the viscoelastic properties from the deformation characteristic of the resilient membrane, utilizing the static and/or transient actuation pressure and the contact force, and
calculate an amplitude ratio, mean ratio and phase difference at different actuation frequencies of the resilient membrane to determine the at least one quantifying parameter,
wherein the amplitude ratio is a ratio of an amplitude of a flow pressure signal and an amplitude of a signal of the at least one force sensor;
wherein the mean ratio is a ratio of a mean of the flow pressure signal divided by a mean of the signal of the at least one force sensor;
wherein the phase difference is a difference between the flow pressure signal and the signal of the at least one force sensor; and
wherein the flow pressure signal corresponds to an input pressure wave inflating and deflating the at least one resilient membrane, and the signal of the at least one force sensor is used to determine the contact force between the apparatus and the at least the portion of the object when engaging the at least the portion of the object during the actuations of the actuator and the resilient membrane.

56. A method for quantifying viscoelastic properties of at least a portion of an object, the method comprising:
(a) operably and engagingly positioning an apparatus to the at least the portion of the object;
(b) activating the apparatus by selectively providing a static and/or transient actuation pressure to the at least the portion of the object via a resilient membrane of the apparatus;
(c) recording a deformation characteristic of the resilient membrane during engagement with the at least the portion of the object;
(d) recording a contact force between the apparatus and the at least the portion of the object during actuation of the resilient membrane using a force sensor, the actuation of the resilient membrane being provided as a result of the activating of the apparatus; and
(e) determining at least one quantifying parameter of the viscoelastic properties from the deformation characteristic of the resilient membrane, utilizing the static and/or transient actuation pressure and the recorded contact force;
the method further comprising calculating an amplitude ratio, mean ratio and phase difference at different frequencies to determine the at least one quantifying parameter,
wherein the amplitude ratio is a ratio of an amplitude of a flow pressure signal and an amplitude of a signal of the at least one force sensor;
wherein the mean ratio is a ratio of a mean of the flow pressure signal divided by a mean of the signal of the at least one force sensor;
wherein the phase difference is a difference between the flow pressure signal and the signal of the at least one force sensor; and
wherein the flow pressure signal corresponds to an input pressure wave inflating and deflating the at least one resilient membrane, and the signal of the at least one force sensor is used to determine the contact force between the apparatus and the at least the portion of the object when engaging the at least the portion of the object during the actuations of the actuator and the resilient membrane.

\* \* \* \* \*